United States Patent [19]
King et al.

[11] Patent Number: 6,153,427
[45] Date of Patent: *Nov. 28, 2000

[54] ERYTHROPOIETIN-INDUCIBLE, ERYTHROID-SPECIFIC DNA CONSTRUCT

[75] Inventors: Donna King, Lake Bluff; Gary B. Schneider, Gurnee, both of Ill.

[73] Assignee: Northeastern Ohio Universities College of Medicine, Rootstown, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/321,686

[22] Filed: Oct. 12, 1994

[51] Int. Cl.⁷ .......................... C12N 15/63; C12N 15/00; C12N 15/09; C12N 5/00
[52] U.S. Cl. ................ 435/320.1; 435/455; 435/69.1; 800/18
[58] Field of Search ..................... 424/520, 577; 536/23.51, 24.1; 514/44, 2; 530/399, 350; 435/69.1, 70.1, 91.4, 172.1, 172.3, 320.1, 325, 355, 372, 375, 455; 800/18

[56] References Cited

U.S. PATENT DOCUMENTS 5,126,260  6/1992  Tuan et al. ........................... 435/240.2

OTHER PUBLICATIONS

R. Behringer et al. Science 245 : 971–3 ('89).
T. Friedmann, Science 244 : 1275–81 ('89).
A. Miller Nature 357 : 455–60 ('92).
A. Miller Blood 76(2) : 271–8 ('90).
J. Chang et al. PNAS 89:3107–10 ('92).
S. McCure et al. N.A.R. 22(21) 4477–81 ('94).
M. Kay et al. 71G 10(7) ('94) 253–7.
R. Milligan Science 260: 926–32 ('93).
NIH Report on Gene Therapy/S.Orkin & A. Motulsky, co–chairs, Dec. 7, 1995.
Houdebine, Journal of Biotechnology, vol. 34, pp. 269–287., 1994.
Cowie et al., Molecular and Cellular Biology, vol. 8, No. 8, pp. 3122–3128, Aug. 1988.
Yu et al., The Journal of Biological Chemistry, vol. 266, No. 14, pp. 8907–8915, 1991.
Schmidt–Wolf et al., Journal of Hematotherapy, vol. 4, pp. 551–561.

*Primary Examiner*—Jasemine Chambers
*Assistant Examiner*—Jill D. Martin
*Attorney, Agent, or Firm*—Calfee, Halter & Griswold LLP

[57] ABSTRACT

An erythropoietin-inducible, erythroid-specific DNA construct is disclosed. The DNA construct comprises a promoter sequence from a sheep juvenile beta globin gene, an erythroid-specific enhancer sequence from the locus control region of the human beta globin gene and a nucleotide coding sequence of interest.

10 Claims, 11 Drawing Sheets

Figure 1A:

The HS 2 + β$^c$hGH transgene

FIG. 1B (SEQ ID No:1)

AAGCTTCAGTTTTTCCTTAGTTCCTGTTACATTTCTGTGTGTCTCC
ATTAGTGACCTCCCATAGTCCAAGCATGAGCAGTTCTGGCCAGGCC
CCTGTCGGGGTCAGTGCCCCACCCCCGCCTTCTGGTTCTGTGTAAC
CTTCTAAGCAAACCTTCTGGCTCAAGCACAGCAATGCTGAGTCATG
ATGAGTCATGCTGAGGCTTAGGGTGTGTGCCCAGATGTTCTCAGCC
TAGAGTGATGACTCCTATCTGGGTCCCCAGCAGGATGCTTACAGGG
CAGATGGCAAAAAAAGGAGAAGCTGACCACCTGACTAAAACTCCA
CCTCAAACGGCATCATAAAGAAAATGGATGCCTGAGACAGAATGTG
ACATATTCTAGAATATATTATTTCCTGAATATATATATATATATATAC
ACATACGTATATATATATATATATATATTTGTTGTTAT
CAATTGCCATAGAATGATTAGTTATTGTGAATCAAATATTTATCTT
GCAGGTGGCCTCTATACCTAGAAGCGGCAGAATCAGGCTTTATTAA
TACATGTGTATAGATTTTAGGATCTATACATGTATTAATATGA
AACAAGGATATGGAAGAGGAAGGCATGAAAACAGGAAAAGAAAACA
AACCTTGTTTGCCATTTTAAGGCACCCTGGACAGCTAGGTGGCAA
AAGGCCTGTGCTGTTAGAGGACACATGCTCACATACGGGTCAGATCT
GACTTGGGGTGCTACTGGGAAGCTCTCATCTTAAGGATACATCT
CAGGCCAGTCTTGGTGCATTAGGAAGATGTAGGCAACTCTGATCCT
GAGAGGAAAGAAACATTCCTCCAGGAGAGCTAAAAGGGTTCACCTG
TGTGGGTAACTGTGAAGGACTACAAGAGGATGAAAAACAATGACAG
ACAGACATAATGCTTGTGGGAGAAAAAACAGGAGGTCAAGGGGATA
GAGAAGGCTTCCAGAAGAATGGCTTTGAAGCTGGCTTCTGTAGGAG
TTCACAGTGGCAAAGATGTTTCAGAAATGTGACATGACTTAAGGAA
CTATACAAAAGGAACAAATTTAAGGAGAGGCAGATAAATTAGTTC
AACAGACATGCAAGGAATTTTCAGATGAATGTTATGTCTCCACTGA
GCTTCTTGAGGTTAGCAGCTGTGAGGGTTTTGCAGGCCCAGGACCC
ATTACAGGACCTCACGTATACTTGACACTGTTTTTTGTATTCATTT
GTGAATGAATGACCTCTTGTCAGTCTACTCGGTTTCGCTGTGAATG
AATGATGTCTTGTCAGCCTACTTGGTTTCGCTAAGAGCACAGAGAG
AAGATTTAGTGATGCTATGTAAAACTTCCTTTTTGGTTCAAGTGT
ATGTTTGTGATAGAAATGAAGACAGGCTACATGATGCATATCTAAC
ATAAACACAAACATTAAGAAAGGAAATCAACCTGAAGAGTATTTAT
ACAGATAACAAAATACAGAGAGTGAGTTAAATGTGTAATAACTGTG
GCACAGGCTGGAATATGAGCCATTTAAATCACAAATTAATTAGAAA
AAAAACAGTGGGGAAAAATTCCATGGATGGGTCTAGAAAGACTAG
CATTGTTTTAGGTTGAGTGGCAGTGTTTAAAGGGTGATATCAGACT
AAACTTGAAATATGTGGCTAAATAACTAGAATACTCTTATTTTTT
CGTATCATGAATAGCAGATATAGCTTGATGGCCCCATGCTTGGTTT
AACATCCTTGCTGTTCCTGACATGAAATCCTTAATTTTTGACAAAG

FIG. 1B (SEQ ID No: 2)

GGGCTATTCATTTTCATTTTATATTGGGCCTAGAAATTATGTAGAT
GGTCCTGAGGAAAAGTTTATAGCTTGTCTATTTCTCTCTAACAT
AGTTGTCAGCACAATGCCTAGGCTATAGGAAGTACTCAAAGCTTCT
CTGTTCTTCCAGACACTTTCACAGGTCAGTCCATGAGGAAACAAAT
TATATGCCTTGATTTAGTCTTTGAACACATTGCCTCTCAGGGTT
ACTGAAACTTTGGGGTTATGATTGAATTTTACTTATTTGTATTTC
TTACTACATGGAGAGGTCTCTACGTTTTCACATATGGATTAATGGA
GTAAGTATTTCACAGGATCTCTCAATCCACACTTATTCTATTTTTC
TATCATTATTCATTTGGTCGTAAATTAAATTAAGAAAAAATTGAAT
GAGTAGATAAGTAAATGAATATTTGTTTTCATACCAGAATGACTTA
ATCCCAAACAGGCGAACAAAGAGATGCATATTTAGAACAGAGGCA
GAAGTTTTATCCATGGTGTCCTTGTAATTCTTTTGCATATTCTGAA
GGCACAGGAGGTGATCCATCCACATAGTCTTAAGTTGAATCATAGT
GTACAAATCCTTTCCACTTTCTGGAGCCCAGATTCTTAATTTGTGT
TATAAAAAATTGAGGAAGTGTTTTCCAAGAGATTACCTCGTTGAG
ATTCTAAAATCTCTACAAGCAAACTTGCTAAGGAAGATGATTTAG
TAGCAATGTGTATTGCTGGAATGACTGAGACCTTGAGATGCCCAGA
AAGAGGGCTGACGGTCTCAAGTCAGTACCAGGAAGACCAAGGAGAA
GTATGACTATCATCATTCAAGCCTCACCCTGTGGAACCACAACTTG
GAATGAGCCAATCTGCTCACAGAAGCAGGGAGGGCAGGAGGCAGGG
CTGGGCATAAAAGGAAGAGCCGGGCCAGGGGGCCCACAAGAGACCG
GCTCAAGGATCCCAAGGCCCAACTCCCCGAACCACTCAGGGTCCTG
TGGACGCTCACCTAGCTGCAATGGCTACAGGTAAGCGCCCCTAAAA
TCCCTTTGGGCACAATGTGTCCTGAGGGGAGAGGCAGCGACCTGTA
GATGGGACGGGGGCACTAACCCTCAGGTTTGGGGCTTCTGAATGAG
TATCGCCATGTAAGCCCAGTATGGCCAATCTCAGAAAGCTCCTGGT
CCCTGGAGGGATGGAGAGAGAAAAACAAACAGCTCCTGGAGCAGGG
AGAGTGCTGGCCTCTTGCTCTCCGGCTCCCTCTGTTGCCCTCTGGT
TTCTCCCCAGGCTCCCGGACGTCCCTGCTCCTGGCTTTTGGCCTGC
TCTGCCTGCCCTGGCTTCAAGAGGGCAGTGCCTTCCCAACCATTCC
CTTATCCAGGCTTTTTGACAACGCTAGTCTCCGCGCCCATCGTCTG
CACCAGCTGGCCTTTGACACCTACCAGGAGTTTGTAAGCTCTTGGG
GAATGGGTGCGCATCAGGGGTGGCAGGAAGGGGTGACTTTCCCCCG
CTGGGAAATAAGAGGAGGAGACTAAGGAGCTCAGGGTTTTTCCCGA
AGCGAAAATGCAGGCAGATGAGCACACGCTGAGTGAGGTTCCCAGA
AAAGTAACAATGGGAGCTGGTCTCCAGCGTAGACCTTGGTGGGCGG
TCCTTCTCCTAGGAAGAAGCCTATATCCCAAAGGAACAGAAGTATT
CATTCCTGCAGAACCCCAGACCTCCCTCTGTTTCTCAGAGTCTAT
TCCGACACCCTCCAACAGGGAGGAAACACAACAGAAATCCGTGAGT
GGATGCCTTGACCCCAGGCGGGGATGGGGGAGACCTGTAGTCAGAG
CCCCCGGGCAGCACAGGCCAATGCCCGTCCTTCCCCTGCAGAACCT

FIG. 1B (SEQ ID No:3)

AGAGCTGCTCCGCATCTCCCTGCTGCTCATCCAGTCGTGGCTGGAG
CCCGTGCAGTTCCTCAGGAGTGTCTTCGCCAACAGCCTGGTGTACG
GCGCCTCTGACAGCAACGTCTATGACCTCCTAAAGGACCTAGAGGA
AGGCATCCAAACGCTGATGGGGGTGGGGGTGGCGCTAGGGGTCCCC
AATCTTGGAGCCCCACTGACTTTGAGAGCTGTGTTAGAGAAACACT
GCTGCCCTCTTTTTAGCAGTCCAGGCCCTGACCCAAGAGAACTCAC
CTTATTCTTCATTTCCCCTCGTGAATCCTCTAGCCTTTCTCTACAC
CCTGAAGGGGAGGGAGGAAAATGAATGAATGAGAAAGGGAGGGAGC
AGTACCCAAGCGCTTGGCCTCTCCTTCTCTTCCTTCACTTTGCAGA
GGCTGGAAGATGGCAGCCCCGGACTGGGCAGATCTTCAAGCAGAC
CTACAGCAAGTTCGACACAAACTCACACAACGATGACGCACTACTC
AAGAACTACGGGCTGCTCTACTGCTTCAGGAAGGACATGGACAAGG
TCGAGACATTCCTGCGCATCGTGCAGTGCCGCTCTGTGGAGGGCAG
CTGTGGCTTCTAGCTGCCCGGGTGGCATCCCTGTGACCCCTCCCCA
GTGCCTCTCCTGGCCTTGGAAGTTGCCACTCCAGTGCCCACCAGCC
TTGTCCTAATAAAATTAAGTTGCATCATTTGTCTGACTAGGTGTC
CTCTATAATATTATGGGGTGGAGGGGGGTGGTTTGGAGCA

FIG. 6B

ERYTHROPOIETIN-INDUCIBLE, ERYTHROID-SPECIFIC DNA CONSTRUCT

TECHNICAL FIELD

The present invention generally relates to the treatment of osteopenias such as osteoporosis, and non-human transgenic mammals expressing therapeutic transgenes for the same.

BACKGROUND OF THE INVENTION

Osteopenias are characterized by decreased mass density and calcification of bone. These diseases are generally attributable to inadequate osteoid synthesis thus causing an imbalance in the bone deposition to resorption ratio. Osteopenias include Paget's disease and primary and secondary osteoporosis. Various treatment protocols have been attempted the objects of which are to stimulate bone formation.

Growth hormone (GH) has been found to stimulate bone formation through stimulation of insulin-like growth factor-1 (IGF-1) production primarily by the liver and secondarily by osteoblasts. Osteoblasts are responsible for synthesis of bone matrix and are known to express osteoblasts are known to express GH receptors. IGF-1 further stimulates osteoblast proliferation. The biological half-lives of IGFs are increased when associated with IGF binding proteins that are also locally produced in the bone. It has been suggested that GH stimulates bone formation through a localized mechanism that increases IGF and IGF binding protein production which in turn stimulates osteoblast proliferation.

Hormonal treatments such as direct infusion of human growth hormone (hGH) have been attempted to stimulate bone deposition. They have not been successful to date. Therapies involving direct GH injections can produce adverse systemic effects. These include sterility or at least reduced fertility and adverse lactogenic effects. Because GH injections induce systemic stimulation of IGFs, which bind insulin receptors when present in excess, severe hypoglycemia may also result.

Attempts have been made to stimulate osteoblasts through localized production of GH in the bone so as to avoid adverse systemic effects through injection of GH. One approach achieved expression of a GH transgene in osteoblasts which stimulated increased growth in the long bones of transgenic mice. (Baker, A. R. et al. (1992) *Mol. Cell. Biol* 12: 5541–47). However, this approach would be difficult to adapt for treatment of osteopenias. After birth, osteoblast isolation from a human patient is highly impractical, thus eliminating use of transfected osteoblasts in any gene therapy. Further, no specific inducible regulatory sequences were included in the transgenic model to provide higher levels of expression, if desired in a given therapy.

Prior to the development of the present invention, no erythroid-specific gene therapy existed for localized and controlled stimulation of GH production to enhance bone deposition using a gene construct which could be up-regulatable based on therapeutic need and capable of being applied to more readily available and collectable tissues, such as bone marrow stem cells.

Erythroid-specific gene expression in transgenic non-human mammals has been previously reported in the art, principally using human beta globin genes. For example, WO 9(1/05041 published Apr. 18, 1991 discloses expression of human beta globin gene in erythroid tissue of transgenic non-human mammals having such expression enhanced through use of selected DNase hypersensitive sites (HS) from the locus control region (LCR) of the human beta globin gene. Palmiter, et al. *Science* 222, 809 (1983) discloses transgenic mice containing the human growth hormone gene fused to a metallothionein promoter sequence. These references neither suggest nor disclose expression of an erythroid-specific gene capable of being up-regulatable in response to therapeutic needs.

A juvenile beta globin gene ($\beta^c$), possessed by artiodactyls (goats and sheep of the haplotype A), exhibits a unique developmental expression pattern. Most mammals have embryonic beta globin genes active early in development. These embryonic genes are then down-regulated in favor of beta globin genes encoding for adult forms of beta globin. Sheep of the A haplotype have a gene switching pattern comprising "embryonic-fetal-juvenile+adult-adult." When mature sheep become anemic or exposed to high altitude, which causes erythropoietin (EPO) levels to rise, the switching pattern can be reversed and $\beta^c$ up-regulated with adult beta globin being down regulated. The juvenile beta globin gene can also be reinduced artificially in healthy adult sheep through administration of EPO.

No gene construct known in the prior art is up-regulatable, erythroid-specific and ligatable to hGH gene for gene therapeutic treatment of osteopenias.

SUMMARY OF THE INVENTION

According to the present invention, a method for the treatment of osteopenias has been developed using a transgene comprising erythroid-specific and up-regulatable $\beta^c$ gene regulatory elements to which hGH gene is ligated. The transgene of the present invention includes, preferably, only the $\beta^c$ promoter with an erythroid-specific enhancer cloned upstream, preferably including at least 5'HS2 from the human beta globin LCR.

Transgenic non-human mammals carrying the transgene of the present invention have been produced that exhibit enhanced but controlled bone deposition in the range of 10%–30% greater than normal. Additional bone deposition may be inducible by up-regulating the transgene through induction of anemia by phenylhydrazine administration or by EPO injections.

In the therapeutic methods of the present invention, a patient's bone marrow tissue, preferably erythroid stem cells, are collected. Next, the stem cells are transfected with the HS2+$\beta^c$hGH transgene and retransfused to repopulate the marrow. Bone marrow stem cells are preferred as they home naturally back to the marrow when reinfused into the bloodstream.

The method of the present invention avoids for the most part the systemic side effects accompanied by injections of recombinant GH by exerting primarily a local effect on bone formation and deposition.

Other advantages and aspects of the present invention will become apparent upon reading the following description of the drawings and detailed description of the invention.

BRIEF DESCRIPTION OF THE DRAWINGS

The file of this patent contains at least one black and white photograph. Copies of this patent with black and white photographs will be provided by the Patent and Trademark Office upon request and payment of the necessary fee.

DETAILED DESCRIPTION

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

Synthesis of HS2+β$^c$hGH Transgene

Figure 1A:
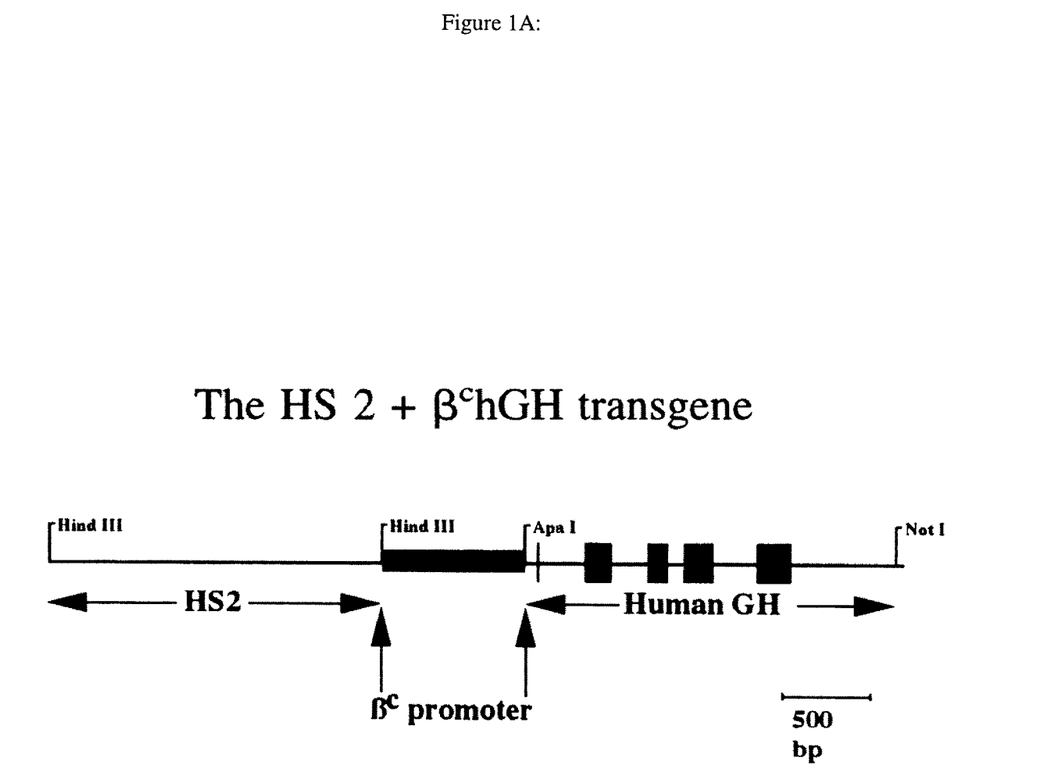
FIG. 1A is a diagrammatic representation of the HS2+$\beta^c$hGH transgene of the present invention.
Figure 1B:
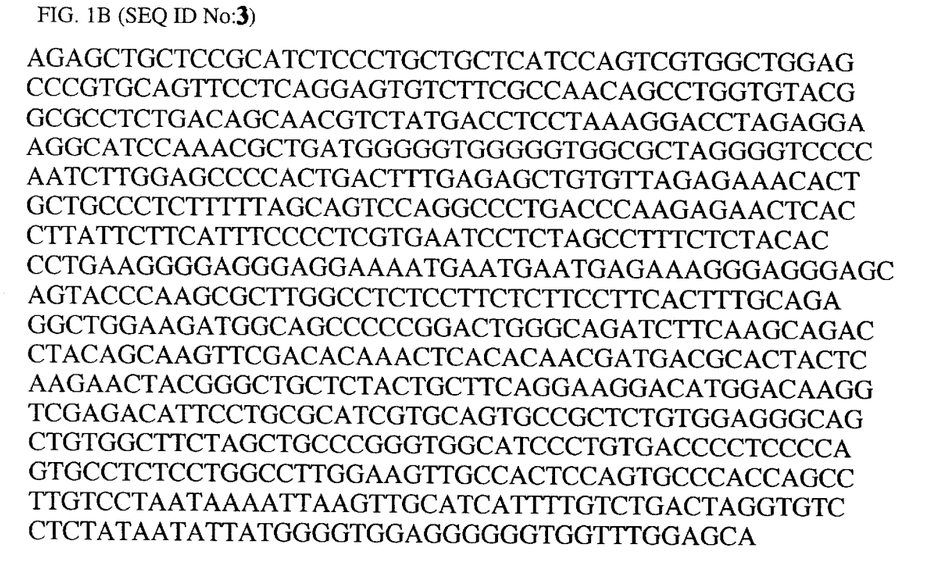
FIG. 1B depicts the nucleotide sequence, SEQ ID No:1, of the HS2+$\beta^c$hGH transgene as cloned.

As disclosed in FIG. 1A, the transgene of the present invention contains three parts: 5'HS2 from the human beta globin LCR, sheep β$^c$ promoter, and hGH gene. The transgene of the present invention embodies the nucleotide sequence, SEQ ID No:1, disclosed in FIG. 1B. The transgene was originally constructed in vector pBS.

The DNA fragment containing the sheep β$^c$ gene is a 3.2 kb Hind III fragment obtained from a plasmid clone available from J. Lingrel, University of Cincinnati; GenBank accession No. X 14728. The sequence for sheep β$^c$ is disclosed in Garner and Lingrel. (1989) *J. Mol. Evol.* 28:175–184 which is incorporated herein by reference in its entirety. This fragment contains the entire β$^c$ gene with 827 bp of 5' flanking sequence and 791 bp of 3' flanking sequence. The β$^c$ promoter is contained in an 819 bp HindIII-PvuII fragment.

The β$^c$ promoter and a small amount of pUC18 vector flanking sequence was purified as a 908 bp DNA fragment. ApaI linkers were blunt-end ligated to this and the fragment was digested with ApaI.

As disclosed in FIG. 1A, the linkered β$^c$ promoter fragment was ligated to the unique ApaI site in the proximal promoter of the hGH gene. The hGH gene, carried in plasmid pghGH2.6-3, was supplied by H. Goodman, Mass. General Hospital. (See also GenBank accession nos. J00148 and K00612) The sequence of hGH gene is disclosed in DeNoto et al. (1981) *Nucl. Acids Res.* 9:3719–3730 which is also incorporated herein by reference in its entirety.

The total length of the promoter used in the transgene construct of the present invention is 842 bp. Of this the β$^c$ promoter contributed 819 bp to the promoter with the balance of the promoter sequence derived from hGH gene itself and the ApaI linker. The cap site and all downstream sequences were derived entirely from the hGH gene.

A 1.9 kb HindIII fragment containing the 5'HS2 element of the human beta globin LCR was inserted into the HindIII site immediately upstream of the β$^c$ promoter to complete the construct. The 5'HS2 HindIII fragment is defined as nucleotides 1527 through 3451 in GenBank file Humhbb-part 3.

Production of Transgenic Mice Containing HS2+ β$^c$hGH Transgene

The transgene of the present invention was purified from vector sequence before microinjection into mouse embryos. No vector sequence was microinjected. After the DNA was purified free of vector sequences and concentrated using Elutip columns (Schleicher and Schuell, Inc.) the purified and concentrated DNA was microinjected into male or female pronuclei of fertilized one-cell mouse eggs using techniques known in the art. DNA is microinjected at a concentration of 2 ng/μl in 10 mM Tris (pH 7.5), 0.1 mM EDTA.

The injected eggs were then implanted into pseudopregnant female mice following the procedures disclosed in Hogan, et al. (1986 Cold Spring Harbor Lab.) *Manipulating the Mouse Embryo, A Laboratory Manual.* The eggs in the foster females were allowed to develop to term, usually 20–21 days.

Mice were obtained from The Jackson Laboratory. Embryos for microinjection were produced by breeding B6SJL/F$_1$J mice. Genomic DNA was purified from tail tissue and transgenic individuals were determined by slot blot hybridization. Transgene integrity was confirmed by genomic Southern blot hybridization.

Analysis of hGH Transgenic Mice

Six HS2+β$^c$hGH transgenic lines were produced by breeding founder mice (TG407, TG409, TG416, TG420, TG435, TG450). The TG420 TG435 and TG450 lines were the primary focus of analysis. Expression of the hGH transgene was analyzed in blood by the quantitative RNase protection assay at key developmental time points.

RNA was prepared for RNase protection assay by collecting blood samples from embryos and fetuses by first dissecting individuals from the uterus in their amniotic sacs, rinsing in cold phosphate-buffered saline (PBS; 0.8% NaCl, 2.7 mM KCl, 1.5 mM $KH_2PO_4$, 20 mM $NA_2HPO_2$) containing 10 units/ml of heparin, and then bleeding each individual from the amnion into fresh cold PBS-heparin. Blood was collected from very young mice into cold PBS-heparin following decapitation. Older mice were bled from the tail vein.

Figure 2:
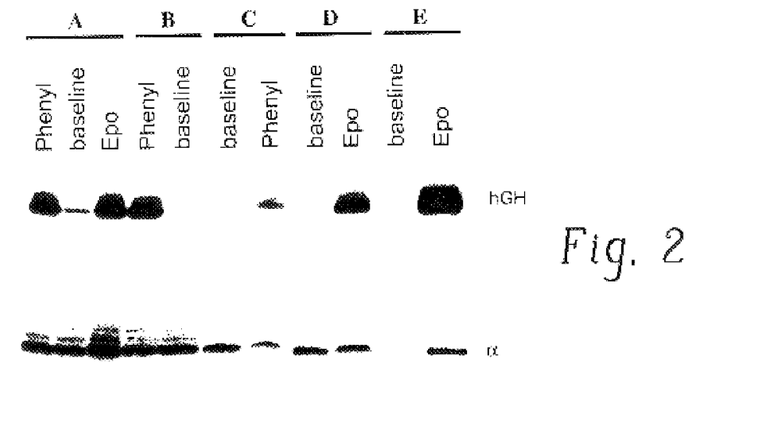
FIG. 2 discloses RNase protection analysis of the TG420 transgenic mouse line showing phenylhydrazine and EPO induction of the transcription of the hGH transgene.

FIG. 2 discloses the results of RNase protection assay using five 5–6 month old mice referred to in FIG. 2 as A through E. Endogenous alpha globin provided the internal standard in each sample. In FIG. 2 the ratio of hGH to alpha globin in the baseline sample is compared to the ratio of hGH to alpha globin in the treated sample to indicate fold induction of the hGH gene.

As disclosed in FIG. 2, the TG420 line was able to up-regulate expression of the transgene in response to phenylhydrazine-induced anemia and EPO. The TG420 line increased expression of hGH mRNA four to eight-fold with phenylhydrazine and three to twenty-fold with EPO induction. The TG435 line induced expression two to 14-fold with these treatments. This suggests that the 819 bp $\beta^c$ promoter fragment that was used contains an "EPO-response element." It presently is unknown in the art what exact DNA sequence comprises an "EPO response element" or how EPO acts through it to induce expression of a gene.

Figure 3A:
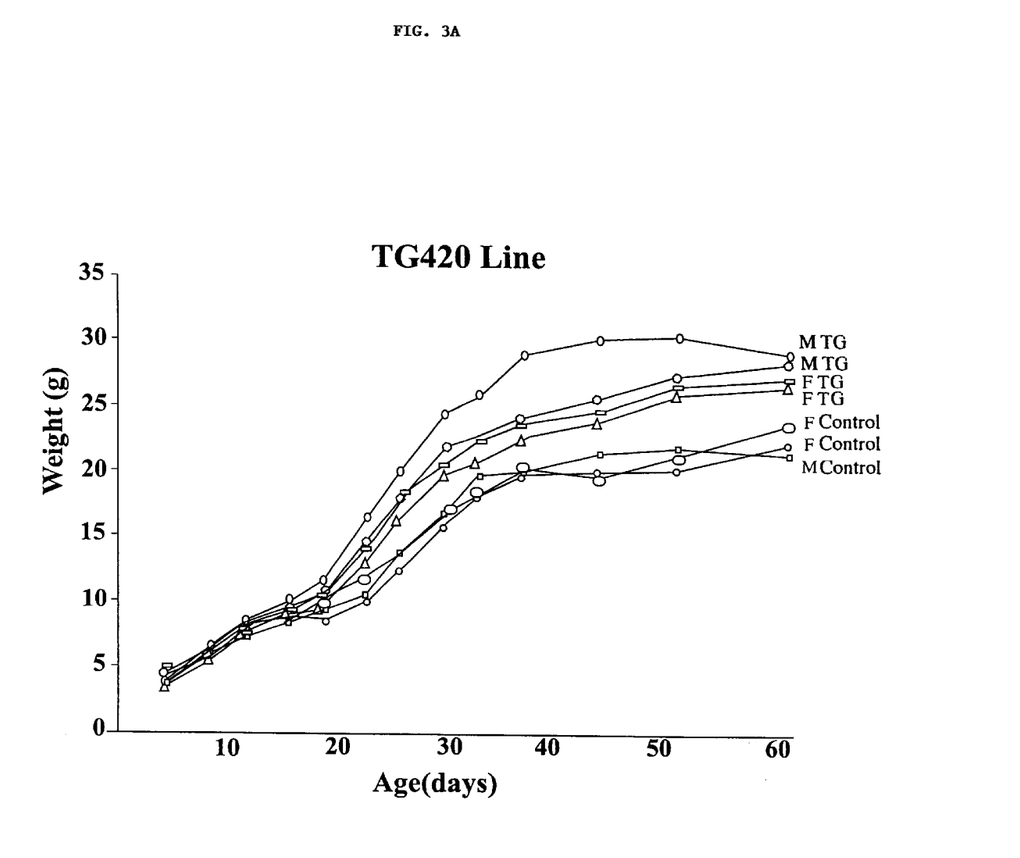
FIGS. 3A–3C are graphic representations disclosing growth rates of the TG420, TG450 and TG435 transgenic lines compared to nontransgenic littermates wherein "M" means male, "F" means female and "TG" means transgenic.
Figure 3B:
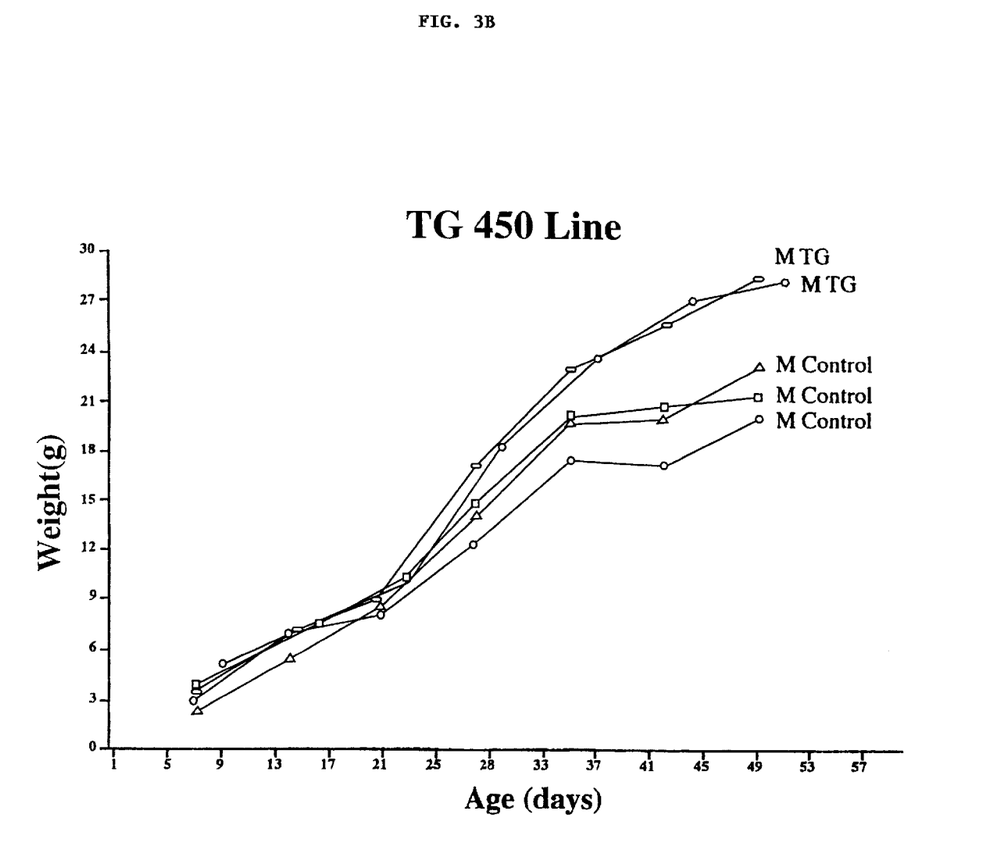
Figure 3C:
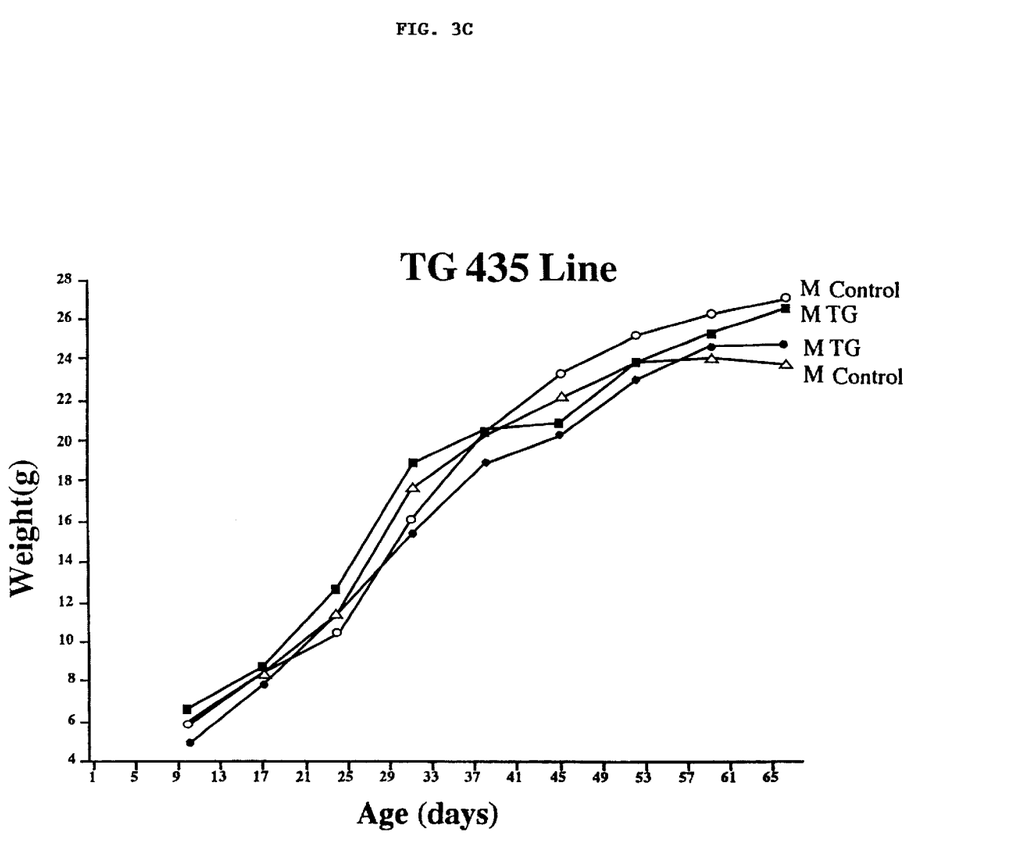

The most dramatic physiological characteristics of the HS2+$\beta^c$hGH transgenic mice is that the mice in three of the lines TG420, TG450, and TG435 grow 5% to 40% larger than normal. Representative plots of transgenic and non-transgenic littermate growth rates are shown in FIGS. 3A through 3C. Although the mice produce their highest levels of hGH mRNA as embryos and fetuses, their enhanced growth does not become apparent until approximately 3 weeks of age. This is most likely due to the absence of GH receptors in the liver preventing full expression of growth hormone's systematic effects via IGF production (Maes et al., 1983, Endocrinology 113: 1325–1332). The same growth trend was reported for mt-GH (metallothionein-growth hormone) transgenic mice (Hammer et al., 1985, Cold Spring Harbor Symp. Ouant. Biol. 50: 379–387). The mice of three other transgenic lines (TG407, TG409 and TG416) express the $\beta^c$hGH transgene at lower levels and do not grow large. Quantitation of their serum hGH levels and comparison to the measurements already made reveal the threshold amount of systemic hGH that produces a growth response.

Radioimmunoassay (RIA) was used to measure hGH levels in the serum and trapped within the red blood cells (rbcs) of the mice. Efforts focused on the two lines showing the most obvious enhanced growth (TG450 and TG420). In these lines hGH levels are approximately 5–10 times greater inside the rbcs than in the serum of TG450 mice and 50–100 times greater in rbcs than serum for TG420 mice (volumetric comparisons), indicating that most of the hGH is probably never released systemically. Although it is difficult to compare directly between RIAs run in different labs using different tracers, it appears that serum levels of hGH are low in our mouse lines when compared to the mt-GH transgenic mice (Palmiter et al., 1982, Nature 300: 611–615). For example, some representative serum hGH values from TG420 mice were 270 ng/ml at 23 days, 110 ng/ml at 13 weeks, and 59 ng/ml at 5 months. This compares to values of 280, 310, $3.2\times10^4$, $5.7\times10^4$, $1.1\times10^5$ ng/ml in Palmiter's mice (ages not specified).

Figure 4:
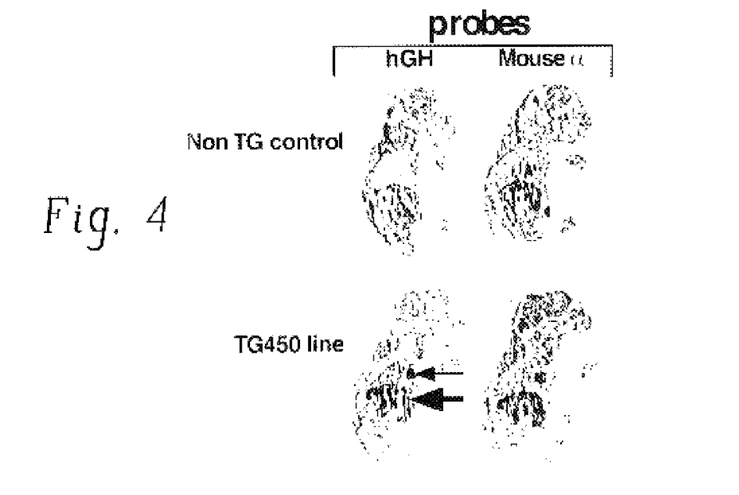
FIG. 4 discloses in situ hybridization of fetal mouse sagittal sections to detect erythroid-specific expression of the transgene of the present invention and endogenous mouse alpha globin in transgenic and nontransgenic control mouse fetuses.

To evaluate tissue specificity of transgene expression in these mice, in situ hybridization studies were conducted. Ten micron sagittal sections of TG and control mouse fetuses were mounted onto nitrocellulose filters and probed with $^{35}$S-labeled antisense hGH or a globin probes. The hGH mRNA specific probe was hybridized to sagittal sections 18.5 gestational day (nearly full-term) mouse fetuses representing the three lines that demonstrated enhanced growth. Adjacent sections were probed for mouse a globin mRNA to identify erythroid tissues and pooled blood. Representative control and transgenic sections are shown in FIG. 4. Fetal liver was hybridized by both a globin and hGH probes indicating expression of both genes in the tissue. Liver is the major erythropoietic organ at this age. Pooled blood produces an a globin signal in the hearts of both TG and nonTG fetuses. By the same token, high hGH mRNA, also present in the blood, is detected in the heart of the TG fetus. The large arrow in FIG. 4 indicates the hybridization signal in liver and the small arrow indicates the heart. Transgenic fetuses from the TG420, TG435 and TG450 lines produced the same results.

Transgenic mice from the TG420 and TG450 lines had spines that from simple observation were unquestionably longer than their littermate controls. To confirm this observation, the bones of both anesthetized live mice and eviscerated carcasses were measured and visualized radiographically by mammography according to the method disclosed in Schneider et al., (1994) J. Bone Min. Res. 9:581–591 which is incorporated herein in its entirety. The development of the vertebrae and knees were monitored from birth through maturity in these two lines and the TG435 line.

Figure 5:
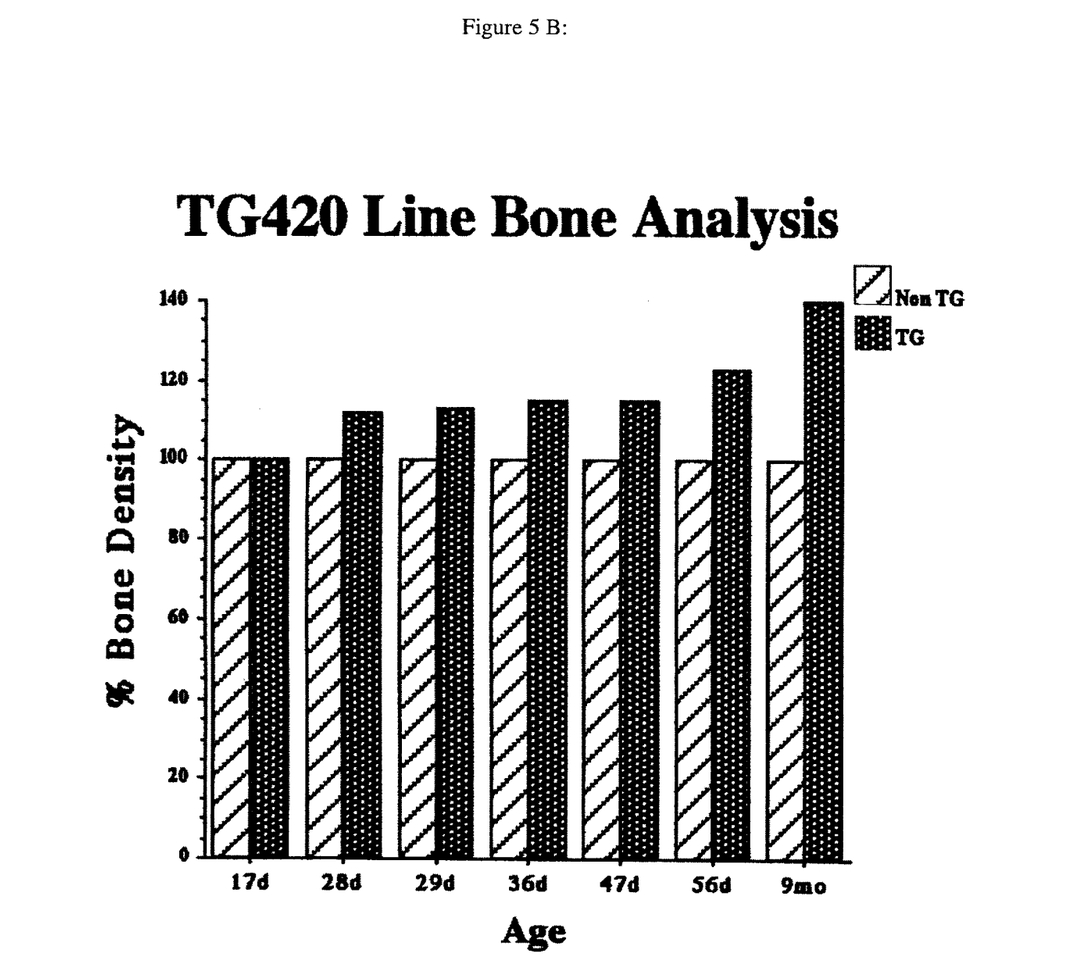
FIG. 5A is a radiographic image comparing representative caudal vertebrae of a male mouse from the TG420 line and an age and sex matched nontransgenic control.
FIG. 5B is a graph comparing cortical bone densities between male mice from the TG420 line and nontransgenic male controls.
Figure 5A:
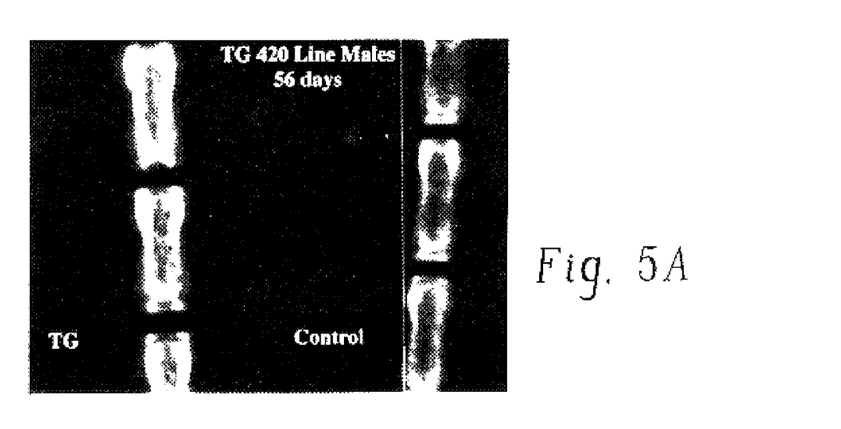

FIG. 5A is a radiographic image of representative caudal vertebrae and FIG. 5B is a graph of relative densities of these vertebrae over time. TG420 and TG450 transgenics have greater bone density than nontransgenics starting around three weeks. The relative difference in density increases with age, despite the extremely how levels of hGH typically measured in the serum of mature transgenics.

For more detailed evaluation of differences due to transgene expression, histological specimens were collected and prepared following the methods disclosed in Schneider, et al.,(1988) J. Bone Min. Res. 3:225–232 which is incorporated in its entirety herein by reference. Cortical bone thickness was measured in some of the oldest members of the mouse colony. Semi-thin sections were prepared from transgenic and age and sex-matched control mice.

Figure 6A:
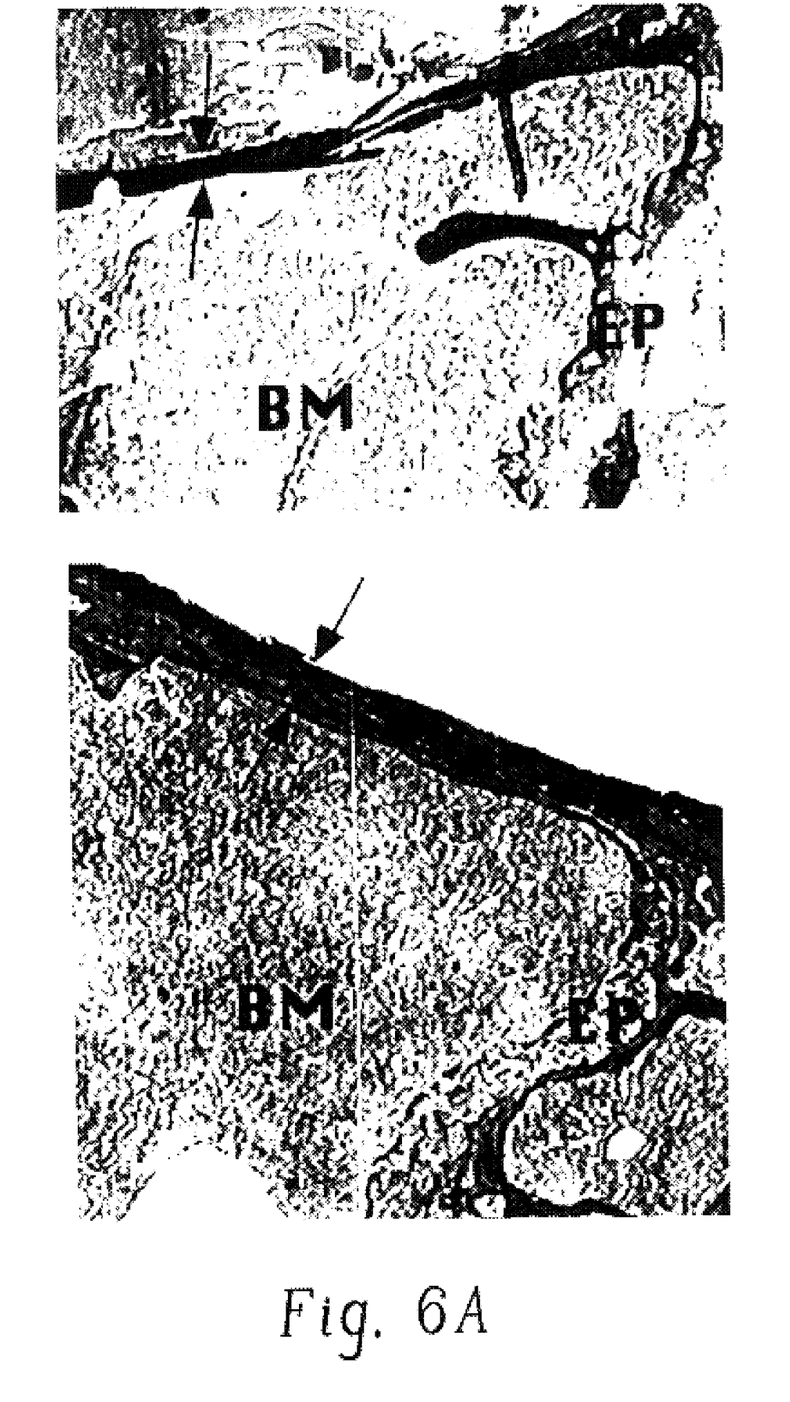
FIG. 6A is stained semi-thin histological sections of proximal tibiae having a nontransgenic control depicted at the top and a male from the TG450 line at the bottom; and, FIG. 6B is a graph comparing average cortical bone thickness between older mice from the TG450 line and nontransgenic age-matched controls.
Figure 6B:
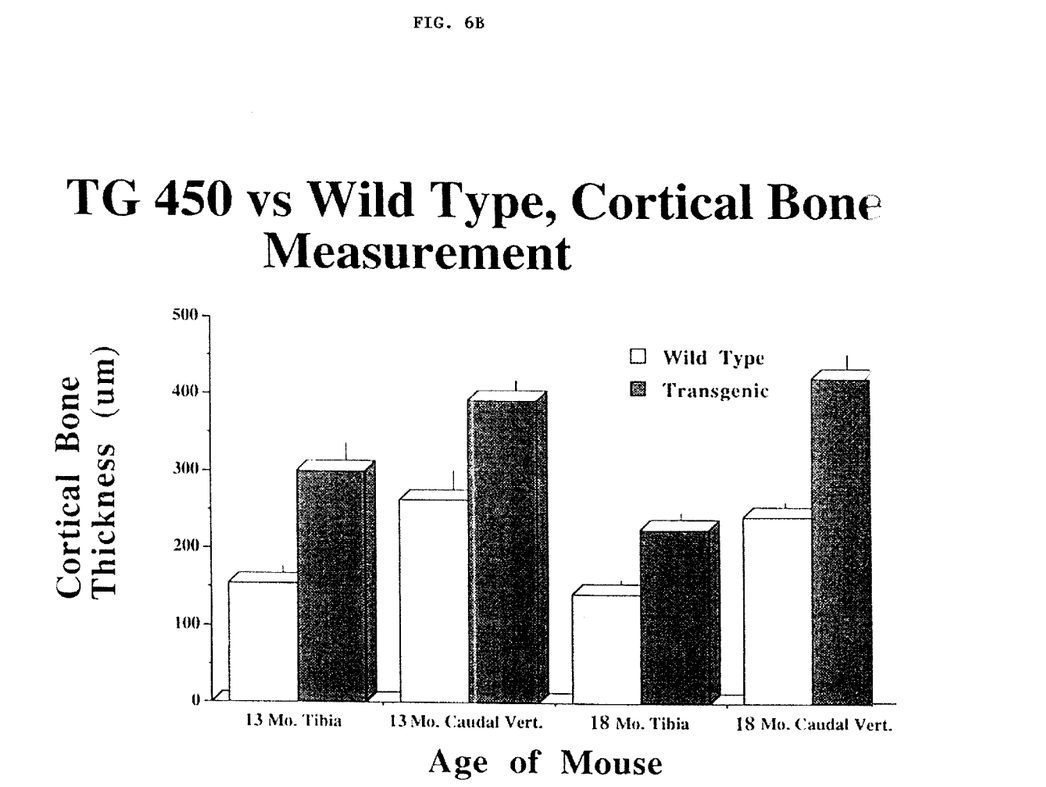

A representative comparison of cortical bone between an age and sex-matched control mouse is shown in FIG. 6A at the top and a 13 month male from the TG450 line is shown in FIG. 6A bottom. As disclosed in FIG. 6B, at 13 and 18 months cortical bone was significantly thicker in the TG450 line.

Gene Therapy Using HS2+$\beta^c$hGH Transgene

The transgene of the present invention has produced dramatic bone development in certain transgenic mice, increasing the thickness and density of the bone. The enhanced bone deposition continues into advanced maturity in the mice, without increasing hGH mRNA in the red blood cells and serum hormone levels in older animals. In many instances, serum hGH levels were within the normal ranges for endogenous mouse growth hormone.

Application of this same delivery mechanism for hGH to humans at risk or suffering from osteoporosis and other osteopenias may improve their bone deposition to resorption ratio. Currently, the most effective treatments for osteoporosis are based on prevention and early warning for those who are especially at risk. The efficacies of current prescriptions such as estrogen, calcium, vitamin supplements, and weight-bearing exercise are sharply reduced when initiated late in life or after menopause.

Gene therapies using the transgene of the present invention would utilize the steps of; collecting a patient's erythroid stem cells from their bone marrow or circulation, the collected stem cells are transfected with an hGH gene construct such as the transgene of the present invention, and the transfected stem cells are retransfused into the patient. They home naturally to the bone marrow compartment in all its locations throughout the body to repopulate the marrow. Individuals identified to be at risk prenatally, e.g. osteogenesis imperfecta patients, could be treated with stem cells isolated from cord blood as well.

Similar gene therapies may be employed in elderly patients who have already experienced fractures or are at serious risk. Likewise, children or young adults with osteopenias or those predisposed to the development of osteopenias could also be treated with transfected erythroid stem cells. The osteopenias include primary osteoporosis such as involutional (postmenopausal and senile) and juvenile osteoporosis and secondary osteoporosis such as those included in Table I below:

TABLE I

Secondary Osteoporosis (Osteopenias)

A. Endocrine
1. Andrenal cortex
   Cushing's disease
   Addison's disease
2. Gonadal disorders
   Hypogonadism
3. Pituitary
   Acromegaly
   Hypopituitarism
4. Pancreas
   Diabetes mellitus
5. Thyroid
   Hyperthyroidism
   Hypothyroidism
6. Parathyroid
   Hyperparathyroidism
B. Marrow replacement and expansion
1. Myeloma
2. Leukemia
3. Metastatic disease
4. Gauchr's disease
5. Amemias (sickle cell, thalassemia)
C. Drugs and substances
1. Corticosteroids
2. Heparin
3. Anticonvulsants
4. Immunosuppressants
5. Alcohol TABLE I-continued Secondary Osteoporosis (Osteopenias)

D. Chronic disease
1. Chronic renal disease
2. Hepatic insufficiency
3. GI malasorption
4. Chronic inflammatory polyarthropathies
5. Chronic debility/immobilization
E. Deficiency states
1. Vitamin D
2. Vitamin C (scurvy)
3. Calcium
4. Malnutrition
F. Inborn errors of metabolism
1. Osteogenesis imperfecta
2. Homocystinuria Therapies using the transgene of the present invention could limit the risk of overuse or unnecessarily high systemic levels of GH.

Deposits

Plasmid containing the HS2+β°hGH transgene have been deposited with the American Type Culture Collection on Oct. 13, 1994 and given ATCC Accession No. 75908.

While the specific embodiments have been illustrated and described, numerous modifications come to mind without significantly departing from the spirit of the invention and the scope of protection is only limited by the scope of the accompanying Claims.

We claim:

1. A DNA construct comprising:
    an erythropoietin inducible promoter sequence from a sheep juvenile beta globin gene;
    an erythroid-specific enhancer sequence operably linked to the promoter sequence, wherein said enhancer sequence comprises a DNase hypersensitive element from the locus control region of the human beta globin gene; and
    a nucleotide coding sequence operably linked to the promoter sequence.

2. The DNA construct of claim 1, wherein the DNase hypersensitive element is the 5'HS2 element.

3. The DNA construct of claim 2, wherein the erythroid-specific enhancer sequence is linked to the 5'end of the promoter sequence.

4. The DNA construct of claim 3, wherein the promoter sequence comprises nucleotide 1926 through nucleotide 2742 of SEQ ID NO: 1, and wherein the erythroid-specific enhancer sequence comprises nucleotide 1 through nucleotide 1925 of SEQ ID NO: 1.

5. The DNA construct of claim 3, wherein the erythroid-specific enhancer sequence is in the same orientation or the reverse orientation as the promoter sequence.

6. A DNA molecule comprising a transgene whose expression is up-regulated in erythroid tissues in a transgenic mouse in response to erythropoietin, said transgene comprising:
    a promoter sequence from a sheep juvenile beta globin gene;
    a nucleotide coding sequence operably linked downstream to the promoter sequence;
    and an erythroid-specific enhancer sequence operably linked to the promoter sequence, wherein said enhancer sequence comprises a DNase hypersensitive element from the locus control region of the human beta globin gene.

7. The DNA molecule of claim 6, wherein the DNase hypersensitive element is the 5'HS2 element, and wherein the nucleotide coding sequence encodes human growth hormone.

8. A DNA molecule comprising:
    the promoter sequence of the sheep juvenile beta globin gene;

an erythroid-specific enhancer sequence comprising a 5'HS2 element from the locus control region of the human beta globin gene operably linked upstream to the sheep juvenile beta globin promoter sequence; and a nucleotide sequence encoding human growth hormone operably linked downstream from the sheep juvenile beta globin promoter sequence.

9. A DNA construct comprising a nucleotide sequence comprising nucleotide 1 through nucleotide 2742 of SEQ ID NO: 1, wherein said nucleotide sequence is in operable linkage with a nucleotide coding sequence.

10. A DNA construct comprising the nucleotide sequence of SEQ ID NO: 1.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 4456 bp
        (B) TYPE: nucleic acid
        (C) STRANDEDNESS: single
        (D) TOPOLOGY: linear (xi) SEQUENCE DESCRIPTION: SEQ ID NO:1:

```
AAGCTTCAGT TTTTCCTTAG TTCCTGTTAC ATTTCTGTGT GTCTCCATTA GTGACCTCCC        60

ATAGTCCAAG CATGAGCAGT TCTGGCCAGG CCCCTGTCGG GGTCAGTGCC CCACCCCCGC       120

CTTCTGGTTC TGTGTAACCT TCTAAGCAAA CCTTCTGGCT CAAGCACAGC AATGCTGAGT       180

CATGATGAGT CATGCTGAGG CTTAGGGTGT GTGCCCAGAT GTTCTCAGCC TAGAGTGATG       240

ACTCCTATCT GGGTCCCCAG CAGGATGCTT ACAGGGCAGA TGGCAAAAAA AAGGAGAAGC       300

TGACCACCTG ACTAAAACTC CACCTCAAAC GGCATCATAA AGAAAATGGA TGCCTGAGAC       360

AGAATGTGAC ATATTCTAGA ATATATTATT TCCTGAATAT ATATATATAT ATATATACAC       420

ATATACGTAT ATATATATAT ATATATATAT TTGTTGTTAT CAATTGCCAT AGAATGATTA       480

GTTATTGTGA ATCAAATATT TATCTTGCAG GTGGCCTCTA TACCTAGAAG CGGCAGAATC       540

AGGCTTTATT AATACATGTG TATAGATTTT TAGGATCTAT ACACATGTAT TAATATGAAA       600

CAAGGATATG GAAGAGGAAG GCATGAAAAC AGGAAAAGAA AACAAACCTT GTTTGCCATT       660
```

-continued

```
TTAAGGCACC CCTGGACAGC TAGGTGGCAA AAGGCCTGTG CTGTTAGAGG ACACATGCTC      720
ACATACGGGG TCAGATCTGA CTTGGGGTGC TACTGGGAAG CTCTCATCTT AAGGATACAT      780
CTCAGGCCAG TCTTGGTGCA TTAGGAAGAT GTAGGCAACT CTGATCCTGA GAGGAAAGAA      840
ACATTCCTCC AGGAGAGCTA AAAGGGTTCA CCTGTGTGGG TAACTGTGAA GGACTACAAG      900
AGGATGAAAA ACAATGACAG ACAGACATAA TGCTTGTGGG AGAAAAAACA GGAGGTCAAG      960
GGGATAGAGA AGGCTTCCAG AAGAATGGCT TTGAAGCTGG CTTCTGTAGG AGTTCACAGT     1020
GGCAAAGATG TTTCAGAAAT GTGACATGAC TTAAGGAACT ATACAAAAG GAACAAATTT      1080
AAGGAGAGGC AGATAAATTA GTTCAACAGA CATGCAAGGA ATTTTCAGAT GAATGTTATG     1140
TCTCCACTGA GCTTCTTGAG GTTAGCAGCT GTGAGGGTTT TGCAGGCCCA GGACCCATTA     1200
CAGGACCTCA CGTATACTTG ACACTGTTTT TTGTATTCAT TTGTGAATGA ATGACCTCTT     1260
GTCAGTCTAC TCGGTTTCGC TGTGAATGAA TGATGTCTTG TCAGCCTACT TGGTTTCGCT     1320
AAGAGCACAG AGAGAAGATT TAGTGATGCT ATGTAAAAAC TTCCTTTTTG GTTCAAGTGT     1380
ATGTTTGTGA TAGAAATGAA GACAGGCTAC ATGATGCATA TCTAACATAA ACACAAACAT     1440
TAAGAAAGGA AATCAACCTG AAGAGTATTT ATACAGATAA CAAAATACAG AGAGTGAGTT     1500
AAATGTGTAA TAACTGTGGC ACAGGCTGGA ATATGAGCCA TTTAAATCAC AAATTAATTA     1560
GAAAAAAAAC AGTGGGAAA AAATTCCATG GATGGGTCTA GAAAGACTAG CATTGTTTTA      1620
GGTTGAGTGG CAGTGTTTAA AGGGTGATAT CAGACTAAAC TTGAAATATG TGGCTAAATA     1680
ACTAGAATAC TCTTTATTTT TTCGTATCAT GAATAGCAGA TATAGCTTGA TGGCCCCATG     1740
CTTGGTTTAA CATCCTTGCT GTTCCTGACA TGAAATCCTT AATTTTTGAC AAAGGGGCTA     1800
TTCATTTTCA TTTTATATTG GGCCTAGAAA TTATGTAGAT GGTCCTGAGG AAAAGTTTAT     1860
AGCTTGTCTA TTTCTCTCTC TAACATAGTT GTCAGCACAA TGCCTAGGCT ATAGGAAGTA     1920
CTCAAAGCTT CTCTGTTCTT CCAGACACTT TCACAGGTCA GTCCATGAGG AAACAAATTA     1980
TATGCCTTGA TTTAGTCTTT GAACACATTG CCTCTCTCAG GGTTACTGAA ACTTTGGGGT     2040
TATGATTGAA TTTTTACTTA TTTGTATTTC TTACTACATG GAGAGGTCTC TACGTTTTCA     2100
CATATGGATT AATGGAGTAA GTATTTCACA GGATCTCTCA ATCCACACTT ATTCTATTTT     2160
TCTATCATTA TTCATTTGGT CGTAAATTAA ATTAAGAAAA AATTGAATGA GTAGATAAGT     2220
AAATGAATAT TTGTTTTCAT ACCAGAATGA CTTAATCCCA AACAGGCGAA CAAAAGAGAT     2280
GCATATTTAG AACAGAGGCA GAAGTTTTAT CCATGGTGTC CTTGTAATTC TTTTGCATAT     2340
TCTGAAGGCA CAGGAGGTGA TCCATCCACA TAGTCTTAAG TTGAATCATA GTGTACAAAT     2400
CCTTTCCACT TTCTGGAGCC CAGATTCTTA ATTTGTGTTA TAAAAAAATT GAGGAAGTGT     2460
TTTCCAAGAG ATTACCTCGT TGAGATTCTA AAATCTCTAC AAGCAAACTT GCTAAGGAAG     2520
ATGATTTTAG TAGCAATGTG TATTGCTGGA ATGACTGAGA CCTTGAGATG CCCAGAAAGA     2580
GGGCTGACGG TCTCAAGTCA GTACCAGGAA GACCAAGGAG AAGTATGACT ATCATCATTC     2640
AAGCCTCACC CTGTGGAACC ACAACTTGGA ATGAGCCAAT CTGCTCACAG AAGCAGGGAG     2700
GGCAGGAGGC AGGGCTGGGC ATAAAAGGAA GAGCCGGGCC AGGGGCCCA CAAGAGACCG      2760
GCTCAAGGAT CCCAAGGCCC AACTCCCCGA ACCACTCAGG GTCCTGTGGA CGCTCACCTA     2820
GCTGCAATGG CTACAGGTAA GCGCCCCTAA AATCCCTTTG GCACAATGT GTCCTGAGGG      2880
GAGAGGCAGC GACCTGTAGA TGGGACGGGG GCACTAACCC TCAGGTTTGG GGCTTCTGAA     2940
TGAGTATCGC CATGTAAGCC CAGTATGGCC AATCTCAGAA AGCTCCTGGT CCCTGGAGGG     3000
```

-continued

```
ATGGAGAGAG AAAAACAAAC AGCTCCTGGA GCAGGGAGAG TGCTGGCCTC TTGCTCTCCG    3060

GCTCCCTCTG TTGCCCTCTG GTTTCTCCCC AGGCTCCCGG ACGTCCCTGC TCCTGGCTTT    3120

TGGCCTGCTC TGCCTGCCCT GGCTTCAAGA GGGCAGTGCC TTCCCAACCA TTCCCTTATC    3180

CAGGCTTTTT GACAACGCTA GTCTCCGCGC CCATCGTCTG CACCAGCTGG CCTTTGACAC    3240

CTACCAGGAG TTTGTAAGCT CTTGGGGAAT GGGTGCGCAT CAGGGGTGGC AGGAAGGGGT    3300

GACTTTCCCC CGCTGGGAAA TAAGAGGAGG AGACTAAGGA GCTCAGGGTT TTTCCCGAAG    3360

CGAAAATGCA GGCAGATGAG CACACGCTGA GTGAGGTTCC CAGAAAAGTA ACAATGGGAG    3420

CTGGTCTCCA GCGTAGACCT TGGTGGGCGG TCCTTCTCCT AGGAAGAAGC CTATATCCCA    3480

AAGGAACAGA AGTATTCATT CCTGCAGAAC CCCCAGACCT CCCTCTGTTT CTCAGAGTCT    3540

ATTCCGACAC CCTCCAACAG GGAGGAAACA CAACAGAAAT CCGTGAGTGG ATGCCTTGAC    3600

CCCAGGCGGG GATGGGGGAG ACCTGTAGTC AGAGCCCCCG GGCAGCACAG GCCAATGCCC    3660

GTCCTTCCCC TGCAGAACCT AGAGCTGCTC CGCATCTCCC TGCTGCTCAT CCAGTCGTGG    3720

CTGGAGCCCG TGCAGTTCCT CAGGAGTGTC TTCGCCAACA GCCTGGTGTA CGGCGCCTCT    3780

GACAGCAACG TCTATGACCT CCTAAAGGAC CTAGAGGAAG GCATCCAAAC GCTGATGGGG    3840

GTGGGGGTGG CGCTAGGGGT CCCCAATCTT GGAGCCCCAC TGACTTTGAG AGCTGTGTTA    3900

GAGAAACACT GCTGCCCTCT TTTTAGCAGT CCAGGCCCTG ACCAAGAGA ACTCACCTTA     3960

TTCTTCATTT CCCCTCGTGA ATCCTCTAGC CTTTCTCTAC ACCCTGAAGG GGAGGGAGGA    4020

AAATGAATGA ATGAGAAAGG GAGGGAGCAG TACCCAAGCG CTTGGCCTCT CCTTCTCTTC    4080

CTTCACTTTG CAGAGGCTGG AAGATGGCAG CCCCCGGACT GGGCAGATCT TCAAGCAGAC    4140

CTACAGCAAG TTCGACACAA ACTCACACAA CGATGACGCA CTACTCAAGA ACTACGGGCT    4200

GCTCTACTGC TTCAGGAAGG ACATGGACAA GGTCGAGACA TTCCTGCGCA TCGTGCAGTG    4260

CCGCTCTGTG GAGGGCAGCT GTGGCTTCTA GCTGCCCGGG TGGCATCCCT GTGACCCCTC    4320

CCCAGTGCCT CTCCTGGCCT TGGAAGTTGC CACTCCAGTG CCCACCAGCC TTGTCCTAAT    4380

AAAATTAAGT TGCATCATTT TGTCTGACTA GGTGTCCTCT ATAATATTAT GGGGTGGAGG    4440

GGGGTGGTTT GGAGCA                                                   4456
```